United States Patent
Grass et al.

(10) Patent No.: US 10,052,032 B2
(45) Date of Patent: Aug. 21, 2018

(54) STENOSIS THERAPY PLANNING

(71) Applicant: KONINKLIJKE PHILIPS N.V., Eindhoven (NL)

(72) Inventors: Michael Grass, Buchholz in der Nordheide (DE); Dirk Schaefer, Hamburg (DE); Holger Schmitt, Luetjensee (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 95 days.

(21) Appl. No.: 14/784,698

(22) PCT Filed: Apr. 16, 2014

(86) PCT No.: PCT/EP2014/057758
§ 371 (c)(1),
(2) Date: Oct. 15, 2015

(87) PCT Pub. No.: WO2014/170385
PCT Pub. Date: Oct. 23, 2014

(65) Prior Publication Data
US 2016/0066795 A1    Mar. 10, 2016

(30) Foreign Application Priority Data
Apr. 18, 2013    (EP) .................................... 13164233

(51) Int. Cl.
*A61B 6/03*    (2006.01)
*A61B 5/02*    (2006.01)
(Continued)

(52) U.S. Cl.
CPC .......... *A61B 5/02007* (2013.01); *A61B 5/026* (2013.01); *A61B 5/0215* (2013.01);
(Continued)

(58) Field of Classification Search
CPC ........ A61B 2019/504; A61B 2019/505; A61B 2019/507; A61B 2019/5289;
(Continued)

(56) References Cited

U.S. PATENT DOCUMENTS 8,157,742 B2    4/2012    Taylor
8,200,466 B2    6/2012    Spilker
(Continued)

FOREIGN PATENT DOCUMENTS

DE    102008014792    6/2009
WO    2004025572    3/2004
(Continued)

OTHER PUBLICATIONS

DeBruyne, B., et al.; Fractional Flow Reserve-Guided PCI versus Medical Therapy in Stable Coronary Disease; 2012; The New England Journal of Medicine; 367(11)991-1001.
(Continued)

*Primary Examiner* — Mark Remaly

(57) ABSTRACT

The present invention relates to stenosis therapy planning. A first volumetric data set is received by medical imaging of at least part of an artery comprising a stenosis. At least one two-dimensional image data (of the stenosis is received. A first arterial pressure drop is determined around the stenosis. A second volumetric data set is generated by registering the at least one two-dimensional image data with the first volumetric data set. A third volumetric data set is generated by simulating a geometry modification of the stenosis in the second volumetric data set and a second arterial pressure drop is estimated around the stenosis in the third volumetric data set.

15 Claims, 4 Drawing Sheets

(51) Int. Cl.
- *A61B 5/0215* (2006.01)
- *A61B 5/026* (2006.01)
- *A61B 5/00* (2006.01)
- A61B 8/14 (2006.01)
- A61B 5/055 (2006.01)
- A61B 90/00 (2016.01)
- A61B 19/00 (2006.01)
- A61B 34/10 (2016.01)

(52) U.S. Cl.
CPC .......... *A61B 5/6851* (2013.01); *A61B 5/742* (2013.01); *A61B 5/055* (2013.01); *A61B 6/032* (2013.01); *A61B 6/037* (2013.01); *A61B 8/14* (2013.01); *A61B 2019/504* (2013.01); *A61B 2019/505* (2013.01); *A61B 2019/507* (2013.01); *A61B 2019/5289* (2013.01); *A61B 2034/105* (2016.02); *A61B 2090/3782* (2016.02)

(58) Field of Classification Search
CPC ........ A61B 2090/3782; A61B 5/02007; A61B 5/0215; A61B 5/026; A61B 5/055; A61B 5/6851; A61B 5/742; A61B 6/032; A61B 6/037; A61B 8/14
See application file for complete search history.

(56) References Cited

U.S. PATENT DOCUMENTS

| | | | |
|---|---|---|---|
| 8,249,815 | B2 | 8/2012 | Taylor |
| 9,814,531 | B2 | 11/2017 | Takanobu |
| 2010/0130878 | A1 | 5/2010 | Lasso |
| 2010/0241404 | A1 | 9/2010 | Taylor |
| 2011/0307231 | A1 | 12/2011 | Kirchner |
| 2012/0022843 | A1 | 1/2012 | Ionasec |
| 2012/0041318 | A1 | 2/2012 | Taylor |
| 2012/0041319 | A1 | 2/2012 | Taylor |
| 2012/0041320 | A1 | 2/2012 | Taylor |
| 2012/0041321 | A1 | 2/2012 | Taylor |
| 2012/0041322 | A1 | 2/2012 | Taylor |
| 2012/0041323 | A1 | 2/2012 | Taylor |
| 2012/0041735 | A1 | 2/2012 | Taylor |
| 2012/0041739 | A1 | 2/2012 | Taylor |
| 2012/0053918 | A1 | 3/2012 | Taylor |
| 2012/0053919 | A1 | 3/2012 | Taylor |
| 2012/0059246 | A1 | 3/2012 | Taylor |
| 2012/0072190 | A1 | 3/2012 | Sharma |
| 2012/0121151 | A1 | 5/2012 | Bernhardt |
| 2012/0243761 | A1 | 9/2012 | Senzig |
| 2013/0090555 | A1 | 4/2013 | Kassab |

FOREIGN PATENT DOCUMENTS

| | | |
|---|---|---|
| WO | 200661814 | 6/2006 |
| WO | 200661815 | 6/2006 |
| WO | 201022762 | 3/2010 |
| WO | 2012011036 | 1/2012 |
| WO | 2012173697 A1 | 12/2012 |

OTHER PUBLICATIONS

Feuchtner, G. M., et al.; Multislice Computed Tomography for Detection of Patients with Aortic Valve Stenosis and Quantification of Severity; 2006; Journal of the American College of Cariology; 47(7)1410-1417.

Neubauer, A. M., et al.; Clinical Feasibility of a Fully Automated 3D Reconstruction of Rotational Coronary X-Ray Angiograms; 2010; Circ. Cardiovasc. Interv.; 3:71-79.

Philips; Interventional X-Ray: Allura 3D-CA; 2004 Koninklijke Philips Electronics N.V. www.healthcare.philips.com/main/products/interventional_xray accessed Aug. 4, 2015.

Tonino, P. A. L., et al.; Fractional Flow Reserve versus Angiography for Guiding Percutaneous Coronary Intervention; 2009; The New England Journal of Medicine; 360:213-224.

STENOSIS THERAPY PLANNING

CROSS-REFERENCE TO PRIOR APPLICATIONS

This application is the U.S. National Phase application under 35 U.S.C. § 371 of International Application No. PCT/EP2014/057758, filed on Apr. 16, 2014, which claims the benefit of European Patent Application No. 13164233.2, filed on Apr. 18, 2013. These applications are hereby incorporated by reference herein.

FIELD OF THE INVENTION

The present invention generally relates to stenosis therapy planning, in particular interventional stenosis therapy planning, such as virtual stenting.

BACKGROUND OF THE INVENTION

Degenerative stenosis is the second most common cardiovascular disease with an incidence of 2-7% in the Western European and North American populations aged beyond 65 years, as described in G. M. Feuchtner, W. Dichtl, et al. "Multislice Computed Tomography for Detection of Patients With Aortic Valve Stenosis and Quantification of Severity", Journal of the American College of Cardiology 2006, 47 (7), 1410-1417. In the context of the present invention the term stenosis represents any abnormal narrowing of an artery. In interventional cardiology a degree of stenosis may be determined using fractional flow reserve (FFR) techniques in which a catheter is introduced into a coronary artery, which is able to measure a relative difference between pressure behind (distal to) and before (proximal to) a stenosis in the artery. Alternatively, medical imaging (such as computed tomography, NMR, PET and the like) may be used as a non-invasive method to determine a degree of stenosis by performing FFR calculations based on reconstructed arterial information. Interventional therapy to treat an arterial stenosis, such as ballooning or stenting, may be applied (directly) after the degree of stenosis is determined. Unfortunately it is not always possible to accurately and/or effectively plan the interventional therapy, since it is not always possible to determine the effect of the therapy beforehand. This may result in non-optimal results or may even require a follow-up interventional procedure, which, in both cases, is not in a patient's best interest.

To assist therapy planning a procedure known as virtual stenting is known in which stent placement is simulated based on determined or modeled artery dimensions and degree of stenosis. U.S. Pat. No. 8,157,742 discloses a procedure in which arterial dimensions and degree of stenosis are determined and modified using a previously obtained computed tomography scan and fractional flow reserves of a stenosed artery and its surroundings.

A drawback of such a procedure is that arterial dimensions and/or degree of stenosis are modeled with insufficient accuracy due to imaging errors (artifacts) and/or because certain assumptions made may be incorrect. Medical imaging of cardiac arteries is particularly complicated and prone to even more artifacts due to constant movement of the cardiac area. Further modeling is necessary to overcome this, for which further assumptions and corrections need to be made, causing further risks of not accurately determining the arterial dimensions and degree of stenosis before or after the virtual stent is placed, and, as a consequence, a physician may not select an optimal treatment.

The method of the present invention provides, amongst others, a solution to the previously stated problem.

SUMMARY OF THE INVENTION

Embodiments according to the present invention are directed to a method for planning an arterial stenosis therapy comprising receiving a first volumetric data set by medical imaging of at least part of an artery, said part comprising a stenosis; receiving at least one two-dimensional image data of the stenosis; determining a first arterial pressure drop around the stenosis; generating a second volumetric data set by registering the at least one two-dimensional image data with the first volumetric data set; generating a third volumetric data set by simulating a geometry modification of the stenosis in the second volumetric data set; and estimating a second arterial pressure drop around the stenosis in the third volumetric data set. In this method three-dimensional imaging data obtained by non-invasive medical imaging of a stenosed artery is combined with a set of two-dimensional images of the same artery, resulting in a data set which represents the actual stenosed artery closer than a data set based on either of the individual data sets. A simulation of modification of a stenosis geometry is more reliable, since the combined data set provides a much more realistic starting point, especially when combined with determined arterial pressure data.

Another embodiment of the present invention is directed towards using the first arterial pressure drop as a starting point in the estimation of the second arterial pressure drop. This allows for an even further improved simulation of the second arterial pressure drop, since it is based on actual arterial pressure data.

Another embodiment of the present invention is directed towards the method further comprising displaying the first arterial pressure drop and the second arterial pressure drop. A user, such as a physician, may immediately see an effect of the geometry modification when the actual and estimated arterial pressure are displayed.

Another embodiment of the present invention is directed towards that the at least one two-dimensional image data comprises at least two two-dimensional image data which were acquired along different projection directions with regard to the stenosis. This allows for imaging at least partially obscured tissue and for improved matching the at least two-dimensional image data with the first volumetric data.

Another embodiment of the present invention is directed towards the method, wherein the geometry modification is a reduction of the stenosis, preferably a removal of the stenosis. Reducing or removing the stenosis corresponds with a desired result of an arterial stenosis therapy and therefore may be used to predict an effect and efficiency thereof.

Another embodiment of the present invention is directed towards the method further comprising generating at least two third volumetric data sets, each of the at least two third volumetric data sets being simulated using a different geometry modification; and simulating the second arterial pressure drop for each of the at least two third volumetric data sets. By simulating pressure drops for different geometry modifications, an effect and efficiency may be simulated for different potential arterial stenosis therapies. A physician may then determine which therapy has a best potential of being successful or most effective.

Another embodiment of the present invention is directed towards the method further comprising displaying each second arterial pressure drop for each of the at least two third volumetric data sets. Displaying all the estimated arterial pressure drops allows a user, such as a physician, to conveniently see the effect of each geometry simulation, which will assist him in select the optimal stenosis therapy.

Another embodiment of the present invention is directed towards the method further comprising a first fractional flow reserve that is calculated from the first arterial pressure drop and a second fractional flow reserve that is calculated from the second arterial pressure drop; and wherein the first fractional flow reserve and the second fractional flow reserve are displayed. A fractional flow reserve is an often used property of arterial flow properties to determine a degree of stenosis. Providing a physician with this information will further assist him to select the optimal arterial stenosis therapy.

Another embodiment of the present invention is directed towards the method, wherein the medical imaging is performed with a medical imaging technique selected from a group comprising computed tomography, position emission tomography, single positron emission computed tomography, magnetic resonance imaging, 3D X-ray imaging, ultrasound imaging, or combinations thereof. These are non-invasive imaging techniques which are available at most hospitals or diagnostic centers.

Another embodiment of the present invention is directed towards the method wherein the modification of the geometry of the stenosis is a narrowing (worsening) of the stenosis. A simulated enlargement may be used to predict how a stenosis might affect flow properties in the artery if the stenosis would remain untreated and worsen.

Still further aspects of the present invention are directed towards a system for planning an arterial stenosis therapy, a computer program product for planning an arterial stenosis therapy and a method for selecting an arterial stenosis therapy.

Still further aspects and embodiments of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

A physician confronted with a patient with a known or suspected arterial stenosis, in particular a coronary artery stenosis, has several treatment options to treat the stenosis by reducing or removing the stenosis, including, but not limited to placing a stent, a ballooning procedure, bypass or other surgery, prescribing medication or a diet, advice lifestyle changes or even take a decision to perform no action at that moment and keep monitoring the situation over time and defer treatment to a later moment in time. If the physician has access to a reliable prediction of an outcome of one or more treatment options, he may better plan and select a most effective treatment.

In the present invention the patient undergoes at least two imaging procedures: a (non-invasive) medical imaging procedure to obtain a volumetric (three-dimensional) data set and a medical imaging procedure to obtain two-dimensional images along different projection directions. Furthermore, an arterial pressure drop is determined around the stenosis, which in the context of the present invention should be interpreted as a difference between a determined arterial pressure before (proximal to) and behind (distal to) the stenosis, wherein both arterial pressures are preferably determined relatively close to the stenosis.

Figure 1:
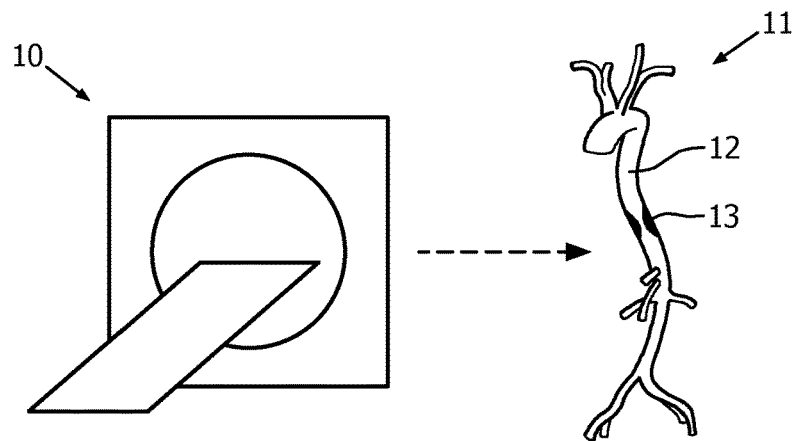
FIG. 1 shows an example of acquisition of volumetric coronary artery stenosis data by medical imaging, in this example with a CT scanner.

FIG. 1 shows a schematic depiction of a medical imager 10 to acquire a volumetric data set, in this embodiment a computed tomography (CT) scanner, but the medical imaging procedure to obtain a volumetric data set may be any other technique known by a person skilled in the art such as, but not limited to position emission tomography (PET), single positron emission computed tomography (SPECT), magnetic resonance imaging (MRI), (3D) X-ray scanning, ultrasound imaging and combinations thereof. A patient is scanned to obtain a volumetric data set, such as a three dimensional image 11 of an artery 12, in this example a coronary artery, comprising a stenosis 13. The volumetric data set may comprise a full scan of the part of the artery and its surroundings or the part of the artery 12 may be segmented from the full scan by segmentation means known to a skilled person in the art. In this embodiment the volumetric data set consists of a segmented part of the artery. Arterial dimensions and stenosis geometry and location may be determined from the volumetric data set.

FIG. 2 shows schematic depictions of medical imagers (20, 20') to acquire at least one two-dimensional image data (21, 21') that may be used as alternatives or in combination. A person skilled in the art would appreciate that in addition to these two examples other invasive or non-invasive medical imaging techniques suitable to obtain two-dimensional image data of a stenosed artery may be used as well. Arterial dimensions and stenosis geometry and location may also be determined from the at least one two-dimensional image data. It is preferred that the at least one two-dimensional image data comprises at least two two-dimensional image data which were acquired along different projection directions with regard to the stenosis. This allows for imaging at least partially obscured tissue and for improved matching the at least two-dimensional image data with the first volumetric data.

Figure 2A:
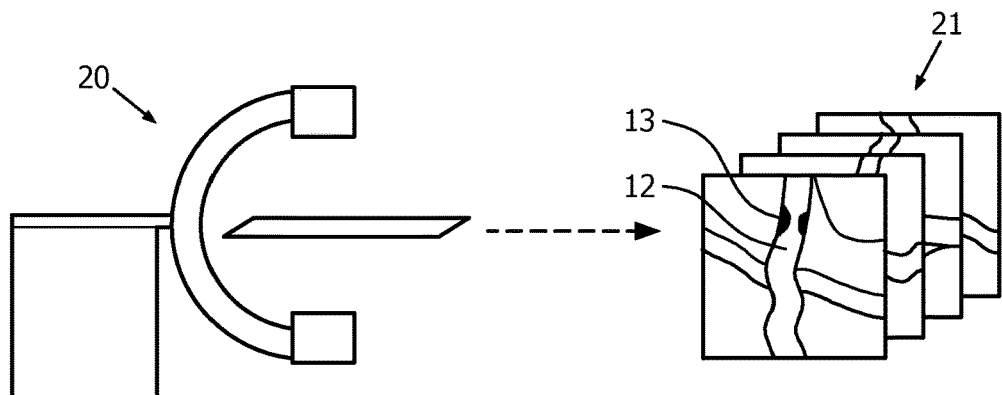
FIG. 2a,b shows two examples of acquisition of two-dimensional data of a stenosis by medical imaging, in these examples with respectively a two-dimensional X-ray imager and in-artery imaging.

In FIG. 2a a two-dimensional X-ray scanner 20 is used to acquire two-dimensional image data 21 from different angles of the stenosis 13 in the artery 12. An advantage of two-dimensional X-ray imaging is its high spatial and temporal resolution and its availability at most suitable medical treatment centers.

Figure 2B:
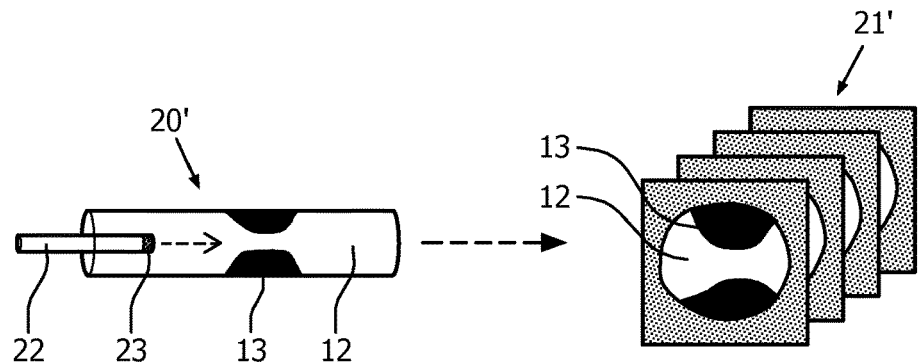

In FIG. 2b in-artery imaging 20' is acquired to obtain two-dimensional image data 21' of the stenosis 13 in the artery 12. In this example a catheter 22 equipped with two-dimensional imaging means 23, for instance ultrasound imaging means or a camera, at its tip is introduced into the coronary artery 12 and guided towards the stenosis 13. The imaging means 23 collects image data of the artery near the stenosis, such as the artery before (proximal to) the stenosis 13, of the stenosis 13 itself and the artery behind (distal to) the stenosis 13. It might be necessary that, if possible, the catheter 22 is introduced from the other side of the artery as well to be able to achieve this. An advantage of in-artery imaging is that actual image data of the stenosed artery is obtained, instead of reconstructed data obtained from non-invasive imaging that may contain artifacts, imaging errors and/or reconstruction errors. Furthermore, a patient is not exposed to possibly damaging irradiation that is inherent with many non-invasive imaging techniques, such as X-ray imaging. Also, in-artery imaging may be less sensitive to movement of the cardiac area, because an in-artery imager moves more or less together with the artery during cardiac movement. And since arterial stenosis therapies often already involve catheterization, the patient may already be prepared for this procedure and the imaging and the therapy may be performed shortly after each other, in one embodiment even with a single multifunctional catheter.

Figure 3:
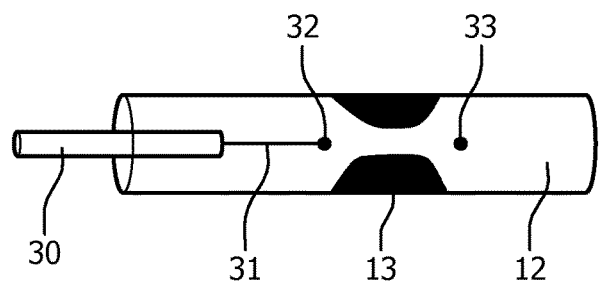
FIG. 3 shows an example of pressure measurement around a stenosis.

FIG. 3 shows an example of measuring arterial pressure around the stenosis using a pressure wire 31. A catheter 30, which may be a multi-functional catheter that also comprises imaging and/or treatment functionality, with pressure wire 31 is introduced into the stenosed artery 12. Arterial pressure is measured in a proximal spot 32 before the stenosis 13 and in a distal spot 33 behind the stenosis 13. Preferably the arterial pressure of the distal spot 33 is measured from the proximal side with the pressure wire extending through the stenosed area to the distal spot 33. If this is not possible, for instance because the stenosis fully or nearly fully blocks the artery 12, the distal spot 33 should be reached from the other side of the artery if possible. Alternatively arterial pressure may also be measured from non-invasive imaging data, but in this case the measurement is in the form of pressure data modeled from image data. An arterial pressure drop is defined and determined as a difference between the measured arterial pressure at the proximal spot (proximal arterial pressure) and the measured arterial pressure at the distal spot (distal arterial pressure). Arterial pressure can be very accurately measured using a pressure wire and provides actual pressure data, instead of modeled pressure data. In an embodiment of the present invention the arterial pressure is determined on multiple distal and/or proximal spots farther away from the stenosis in the artery and/or in connected arteries of an arterial tree, such that a pressure map may be obtained throughout the artery and/or the arterial tree to determine effects of the stenosis in areas that are more remote from the stenosis.

A fractional flow reserve may be determined using the measured proximal and distal arterial pressure. The fractional flow reserve is an often used arterial flow property to determine a degree of stenosis that is defined as a ratio between the distal arterial pressure and the proximal arterial pressure. Providing a physician with this information will further assist him to select an optimal arterial stenosis therapy.

A processor is configured to receive information comprising the volumetric data set as a first volumetric data set, the at least one two-dimensional image data along different projections, the pressure drop as a first pressure drop, and, optionally, the fractional flow reserve as a first fractional flow reserve and/or further image or other relevant data. The processor may receive some or all information from the medical imagers and, if applicable, measurement devices in real-time during imaging or shortly after imaging or measuring. The processor may also receive some or all of the information from a database on which said some or all information may have been previously stored from previously acquired medical imaging procedures and/or measurements.

The processor is further configured to generate a second volumetric data set by registering the at least one two-dimensional image data with the first volumetric data set. This allows for an improved volumetric data set, since artifacts and/or imaging errors or inclarities in the first volumetric data set may be checked against other imaging data, and consequently corrected. Imaging data obtained by in-artery imaging that represents an actual situation is particularly useful in this respect.

Figure 4:
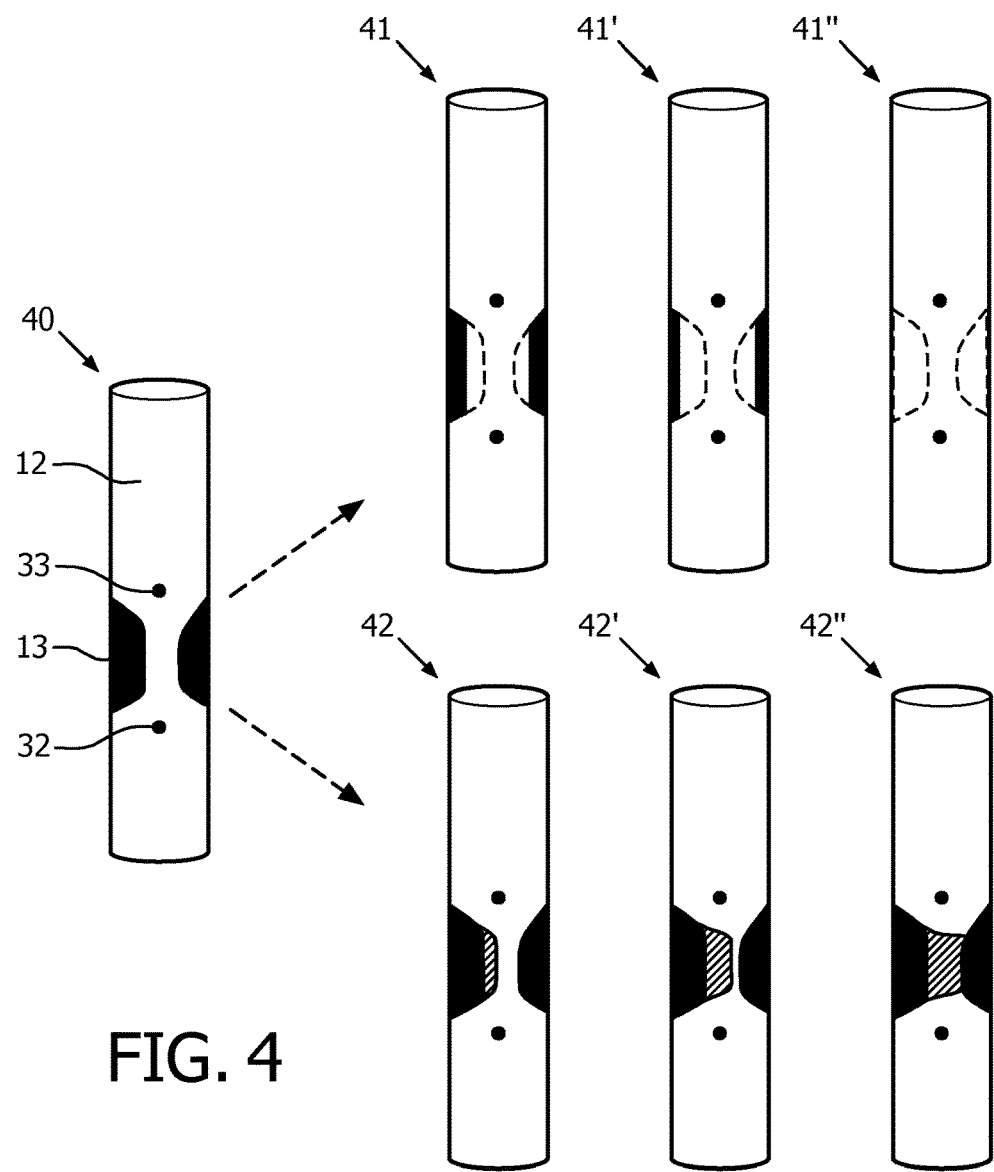
FIG. 4 shows various geometry modifications of a stenosis therapy according to embodiments of the present invention.

The processor is further configured to generate a third volumetric data set by simulating a geometry modification of the stenosis in the second volumetric data set. FIG. 4 shows various examples of such a geometry modification. In this figure a schematic graphical depiction is shown of the second volumetric data set 40 comprising the part of the artery 12 with stenosis 13 and the proximal spot 32 and the distal spot 33 where the arterial pressure was measured. The geometry of the stenosis may be modified by modeling a partial or complete reduction of the stenosis (depicted in the figure by an area with a dashed line representing a section that was removed from the stenosis) to obtain a third volumetric data set 41, 41', 41". This simulates an effect of a selected stenosis therapy, such as placing a stent, a ballooning procedure or another procedure. The geometry reduction may be tuned to a particular therapy, such as different sized stents or balloons. It may also serve as providing a baseline for an effect over time of a possible treatment by medication to reduce the stenosis.

Alternatively the geometry modification may be a further narrowing (worsening) of the stenosis to reduce or even close a throughway through the artery (depicted in the figure by a dashed area that represent a section that was added to the stenosis) to obtain a third volumetric data set 42, 42', 42" or the arterial tree. This may be used to predict an effect over time in case the stenosis is not treated, which could provide valuable information to the physician and the patient about an urgency of the need to treat the stenosis.

The processor is further configured to estimate a second arterial pressure drop around the stenosis 13 in the third volumetric data set 41, 41', 41", 42, 42', 42". In the case of a fully removed stenosis simulation the term 'pressure drop around the stenosis' should be interpreted as the 'pressure drop around the former location of the stenosis'. The second arterial pressure drop may be estimated by modifying, for instance scaling, the first pressure drop based on a change in an arterial diameter at the stenosis location due to the geometry modification. Alternatively, the second arterial pressure drop may be estimated by estimating a new proximal and distal arterial pressure in a situation after the geometry modification. A second fractional flow reserve may be calculated based on the second arterial pressure drop. Estimation of the second arterial pressure drop is much more reliable, because it is based on a more reliable volumetric data set which provides an improved starting point for the estimation that is much closer to a real situation than in the case where the second arterial pressure drop is estimated from just the first volumetric data set or two-dimensional image data.

In a further embodiment of the present invention the processor may be configured to generate at least two third volumetric data sets, wherein each of the at least third volumetric data sets is simulated using a different geometry modification. For each of the at least geometry modification a second arterial pressure drop, and optionally, a second fractional flow reserve, is estimated. This allows providing information regarding various potential arterial stenosis therapies that are pre-selected by the physician. The processor may therefore be configured to receive input from preset or physician-suggested arterial stenosis therapies.

The processor may be further configured to display the first arterial pressure drop and the second arterial pressure drop or drops (and/or the second fractional flow reserve or reserves). This may be displayed on a display device (which may be a monitor, a print-out or any other suitable display device) in numerical, graphical or any other useful form to provide the physician with a clear and reliable prediction of the effect of one or more arterial stenosis therapies. Alternatively, the processor may be further configured to process the first arterial pressure drop and the second arterial pressure drop or drops (and/or the second fractional flow reserve or reserves) for further calculation.

Figure 5:
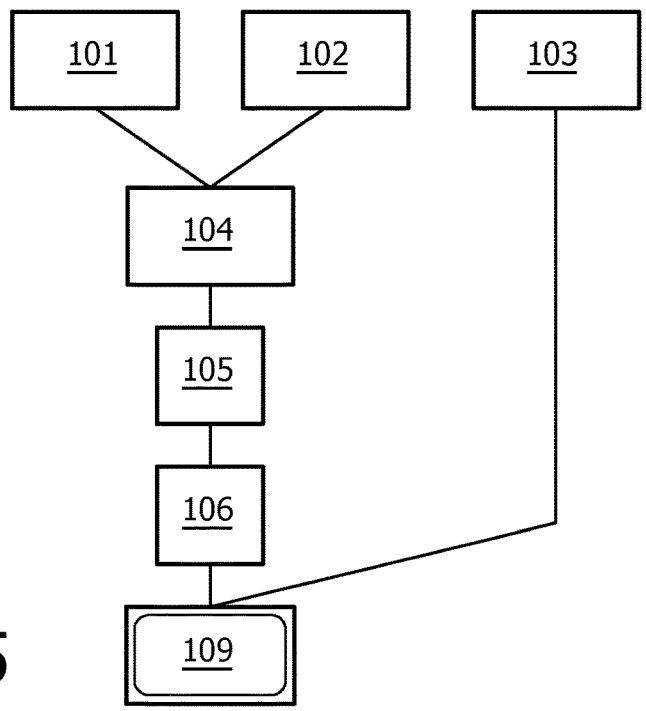
FIG. 5 shows a method for planning an arterial stenosis therapy of an embodiment according to the present invention.

FIG. 5 shows a schematic representation of an embodiment of a method for planning an arterial stenosis therapy according to the present invention. In step 101 a first volumetric data set of at least part of an artery comprising a stenosis and in step 102 at least one two-dimensional image data along different projection directions of the stenosis is received. In step 103 a first arterial pressure around the stenosis is determined. In step 104 a second volumetric data set is generated by registering the at least one two-dimensional image data with the first volumetric data set. In step 105 a third volumetric data set is generated by simulating a geometry modification of the stenosis in the second volumetric data set. In step 106 a second arterial pressure drop around the stenosis in the third volumetric data set is estimated. In step 109 the first arterial pressure drop and the second arterial pressure drop are displayed. Alternatively step 109 may be omitted and replaced by further processing of the first and second arterial pressure drops.

Figure 6:
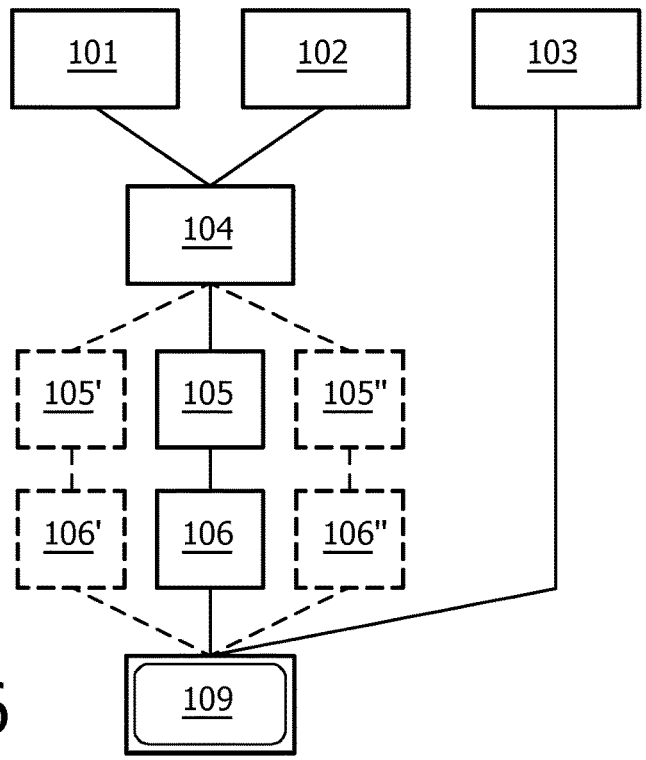
FIG. 6 shows an alternative method for planning an arterial stenosis therapy of an embodiment according to the present invention.

FIG. 6 shows a schematic representation of an extension of the embodiment of FIG. 5. In this case two further third volumetric data sets are generated in steps 105' and 105", for which, in steps 106' and 106", for each a second arterial pressure is estimated. It is of course also possible to generate just one or more than two further third volumetric data sets and to estimate a second arterial pressure for each. In step 109 the first pressure drop and each estimated second pressure drop is displayed.

Figure 7:
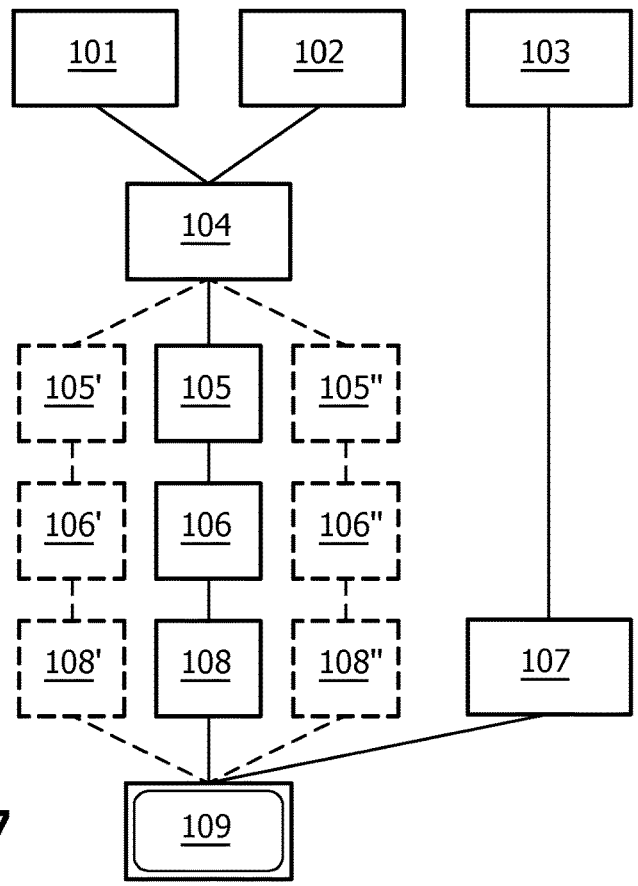
FIG. 7 shows a further alternative method for planning an arterial stenosis therapy of an embodiment according to the present invention.

FIG. 7 shows a schematic representation of another extension of the embodiment of FIGS. 5 and 6. In this case fractional flow reserve is calculated from the second pressure drop in step 108 and displayed in step 109. Of course a fractional flow reserve may be calculated (steps 108', 108") and displayed for further third volumetric data sets.

The methods described above and other similar or related embodiments may be provided as instructions for a computer program product, which are executed when the computer program product is run on a computer.

Figure 8:
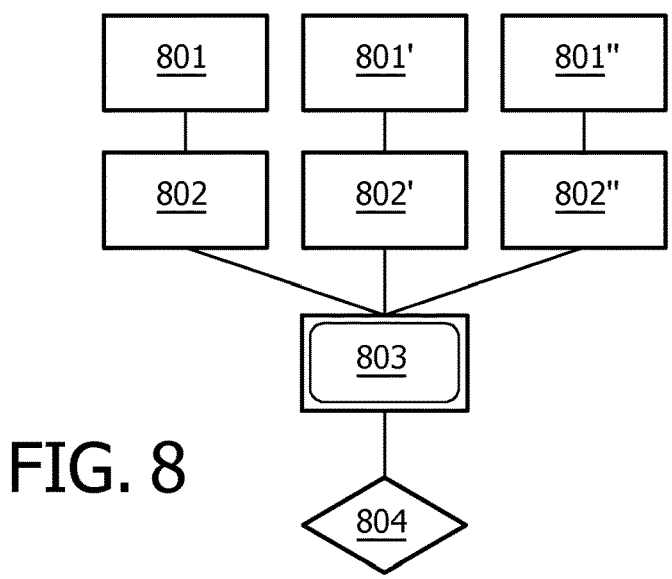
FIG. 8 shows a method for selecting an arterial stenosis therapy of an embodiment according to the present invention.

FIG. 8 shows a schematic representation of a method for selecting an arterial stenosis therapy. A physician may pre-select one or more arterial stenosis therapies (step 801, 801', 801") and perform the method of the embodiment of FIG. 5, 6 or 7 or variations thereof (step 802, 802', 802") for each of the therapies. The first volumetric data set, the at least one two dimensional image and the first arterial pressure drop need not to be received more than once, since these form the same base data for all the calculations for each of the pre-selected therapies. The geometry modification and second pressure drop estimation (and, optionally, the second fractional flow calculation) are performed according to each of the selected arterial stenosis therapies. The first arterial pressure drop and the second arterial pressure drop (and, optionally, the second fractional flow reserve) for each of the selected arterial stenosis therapies are displayed (in step 803) or used for further processing. In step 804 the physician selects the arterial stenosis therapy based on the results he is provided with. He may either select one of the pre-selected therapies or decide to select another therapy, for which he still may perform the method of the embodiment of FIG. 5.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system, comprising:
   a processor configured to
   receive a first volumetric data set of at least part of an artery, said part comprising a stenosis, wherein the first volumetric data set is generated by a computed tomography scanner;
   receive at least one two-dimensional data of the stenosis;
   receive first arterial pressure drop information, said first arterial pressure drop information being an arterial pressure drop around the stenosis;
   register the first volumetric data set with the at least one two-dimensional data to obtain a second volumetric data set;
   modify a geometry of the stenosis in the second volumetric data set which generates a third volumetric data set; and
   estimate a second arterial pressure drop around the geometrically modified stenosis in the third volumetric data set by modifying the first pressure drop based on a change in diameter of the artery or by estimating a proximal and a distal arterial pressure relative to the stenosis after the geometry modification.

2. The system according to claim 1 wherein, the processor is configured to use the first arterial pressure drop as a starting point to estimate the second arterial pressure drop.

3. The system according to claim 1, further comprising:
a display device comprising at least one selected from a group comprising of a monitor and a printout; and
wherein the processor is further configured to display the first arterial pressure drop and the second arterial pressure drop on the display device.

4. The system according to claim 1, the processor further configured to generate at least two third volumetric data sets, each of the at least two third volumetric data sets being simulated using a different geometry modification; and to estimate the second arterial pressure drop for each of the at least two third volumetric data sets; and wherein the processor is further configured to display the second arterial pressure drop for each of the at least two third volumetric data sets on the display device.

5. The system according to claim 1, wherein the processor is further configured to calculate a first fractional flow reserve from the first arterial pressure drop and a second fractional flow reserve from the second arterial pressure drop; and the processor is further configured to display the first fractional flow reserve and the second fractional flow reserve on the display device.

6. The system according to claim 1, wherein the geometry modification is a reduction of the geometry of the stenosis, preferably a removal of the stenosis.

7. A method, comprising
receiving a first volumetric data set by medical imaging of at least part of an artery, said part comprising a stenosis, wherein the first volumetric data set is generated by a computed tomography scanner;
receiving at least one two-dimensional image data of the stenosis;
determining a first arterial pressure drop around the stenosis as a difference between a determined arterial pressure proximal to the stenosis and a determined arterial pressure distal to the stenosis;
generating a second volumetric data set by registering the at least one two-dimensional image data with the first volumetric data set;
simulating a geometry modification of the stenosis in the second volumetric data set which generates a third volumetric data set; and
estimating a second arterial pressure drop around the geometrically modified stenosis in the third volumetric data set by modifying the first pressure drop based on a change in diameter of the artery or by estimating a difference between a proximal and a distal arterial pressure relative to the stenosis after the geometry modification.

8. The method according to claim 7, wherein the first arterial pressure drop information was determined from
non-invasive imaging data; or from
data received from a catheter comprising a pressure wire to measure a pressure drop around the stenosis; said measured pressure drop forming the first pressure drop information.

9. The method according to claim 7, wherein the first arterial pressure drop is used as a starting point in the estimation of the second arterial pressure drop.

10. The method according to claim 7, further comprising displaying the first arterial pressure drop and the second arterial pressure drop.

11. The method according to claim 7, wherein the at least one two-dimensional image data comprises at least two two-dimensional image data which were acquired along different projection directions with regard to the stenosis.

12. The method according to claim 7, wherein the geometry modification is a reduction of the stenosis, preferably a removal of the stenosis.

13. The method according to claim 7, further comprising:
generating at least two third volumetric data sets, each of the at least two third volumetric data sets being simulated using a different geometry modification; and
simulating the second arterial pressure drop for each of the at least two third volumetric data sets.

14. The method according to claim 13, further comprising displaying each second arterial pressure drop for each of the at least two third volumetric data sets.

15. A non-transitory computer storage medium comprising instructions which when executed cause one or more processor to perform the steps of the method according to claim 7.

* * * * *